(12) United States Patent
Sharkey et al.

(10) Patent No.: US 11,090,164 B2
(45) Date of Patent: Aug. 17, 2021

(54) KNEE JOINT IMPLANT

(71) Applicant: CORENTEC CO. LTD., Chungcheongnam-do (KR)

(72) Inventors: Peter F. Sharkey, Villanova, PA (US); Javad Parvizi, Gladwyne, PA (US)

(73) Assignee: Corentec Co. Ltd., Chungcheongnam-do (KR)

(*) Notice: Subject to any disclaimer, the term of this patent is extended or adjusted under 35 U.S.C. 154(b) by 447 days.

(21) Appl. No.: 15/720,773

(22) Filed: Sep. 29, 2017

(65) Prior Publication Data

US 2018/0098857 A1   Apr. 12, 2018

Related U.S. Application Data

(60) Provisional application No. 62/407,316, filed on Oct. 12, 2016.

(51) Int. Cl.
| | |
|---|---|
| *A61F 2/38* | (2006.01) |
| *A61F 2/36* | (2006.01) |
| *A61F 2/30* | (2006.01) |
| *A61F 2/46* | (2006.01) |
| *A61B 17/15* | (2006.01) |
| *A61B 17/17* | (2006.01) |
| *A61B 17/88* | (2006.01) |
| *A61B 17/02* | (2006.01) |

(52) U.S. Cl.
CPC .......... *A61F 2/3886* (2013.01); *A61B 17/154* (2013.01); *A61B 17/155* (2013.01); *A61B 17/157* (2013.01); *A61B 17/1764* (2013.01); *A61F 2/30771* (2013.01); *A61F 2/38* (2013.01); *A61F 2/389* (2013.01); *A61F 2/3859* (2013.01); *A61F 2/46* (2013.01); *A61F 2/4684* (2013.01); *A61B 17/88* (2013.01); *A61B 2017/0268* (2013.01); *A61F 2002/30606* (2013.01); *A61F 2002/30883* (2013.01); *A61F 2002/3895* (2013.01)

(58) Field of Classification Search
CPC .......... A61F 2/3886; A61F 2/38; A61F 2/389; A61F 2/3877; A61F 2/3859; A61F 2002/30606; A61F 2002/30883; A61F 2002/3895; A61F 2017/0268
USPC .......... 623/20.14–20.36; 606/88–89
See application file for complete search history.

(56) References Cited

U.S. PATENT DOCUMENTS

| | | | |
|---|---|---|---|
| 4,211,228 A | | 7/1980 | Cloutier |
| 5,037,423 A | | 8/1991 | Kenna |
| 6,102,954 A | * | 8/2000 | Albrektsson ....... A61B 17/8605 623/20.32 |
| 7,094,241 B2 | | 8/2006 | Hodorek et al. |
| 8,167,888 B2 | | 5/2012 | Steffensmeier |
| 2002/0198530 A1 | | 12/2002 | Sanford et al. |
| 2004/0097951 A1 | | 5/2004 | Steffensmeier |
| 2006/0111726 A1 | | 5/2006 | Felt et al. |
| 2010/0249788 A1 | | 9/2010 | Roche |
| 2011/0004316 A1 | | 1/2011 | Murray et al. |

(Continued)

FOREIGN PATENT DOCUMENTS

WO   WO 2005/051240 A1 * 6/2005 ............... A61F 2/38

*Primary Examiner* — Jessica Weiss
(74) *Attorney, Agent, or Firm* — Workman Nydegger

(57) ABSTRACT

A knee joint implant is capable of resolving issues of conventional cementless or uncemented implants. The knee joint implant improves fixing force of the implant in a vertical direction and provides improved initial fixation for the implant.

10 Claims, 18 Drawing Sheets

(56) References Cited

U.S. PATENT DOCUMENTS

| | | | |
|---|---|---|---|
| 2012/0116524 A1* | 5/2012 | Walker | A61F 2/3859 623/20.35 |
| 2012/0259335 A1 | 10/2012 | Scifert et al. | |
| 2013/0035694 A1 | 2/2013 | Grimm et al. | |
| 2015/0374386 A1 | 12/2015 | Collazo et al. | |
| 2016/0008136 A1* | 1/2016 | Jones | A61F 2/389 623/20.17 |

* cited by examiner

KNEE JOINT IMPLANT

CROSS-REFERENCE TO RELATED APPLICATIONS

This application claims the benefit of U.S. Provisional Application No. 62/407,316, filed Oct. 12, 2016, which is incorporated herein by specific reference.

TECHNICAL FIELD

The present invention relates to a knee joint implant and, more specifically, to a knee joint implant capable of resolving issues conventional cementless or uncemented implants possess. The knee joint implant according to the present invention improves fixing force of the implant in a vertical direction and provides improved initial fixation for the implant.

BACKGROUND

A knee joint denotes a joint formed by three bones, which are a femur, a tibia, and a patella, surrounding a knee. The knee joint provided in the left and right legs supports a person's weight and is a key joint for walking, running, or the like. Since the knee joint is frequently used and may be overly worked, the number of patients with incurable knee joints is increasing due to conditions, such as wear of the knee joint, aging of bone tissues, and accidents.

Disease symptoms of the knee joint may appear without any particular external injury, and its cause is usually structural and functional abnormality in patellofemoral joint. Osteomalacia of articular cartilage may be caused by repetitive application of excessive forces to the patellofemoral joint when legs are abnormally bent outward or foot are severely turned out. Weakening of a quadriceps femoris muscle may be a problem when the knee joint has not been used for a long period of time.

One treatment, such as an orthosis that can stabilize the knee joint, may be used when there is structural abnormality in the patellofemoral joint. Moreover, another treatment, such as a surgical treatment where a native knee joint is replaced with an artificial knee joint, may be employed when the damage is severe. Recently, a surgical procedure for replacing an artificial knee joint has been widely performed to patients with incurable knee joint area which is seriously damaged. Two types of such surgical procedures are Unilateral Knee Arthroplasty (UKA) and Total Knee Arthroplasty (TKA), depending on partial or total replacement. Moreover, Bicruciate retaining TKA (BCR) is one type of TKA, where anterior cruciate ligament (ACL) is preserved. BCR has advantages of natural knee motion, improved range of motion (ROM), and improved joint functions.

Due to limited exposure and lack of access to the posterior aspect of the knee, an optimal cement technique is challenging. Also, because surgeons often use a limited amount of PMMA during TKA, initial implant fixation is less than optimal. For these reasons, cementless TKA has relative advantages. In particular, uncemented implant fixation of cementless TKA can cause bone remodeling with structural enhancement and reduce a possibility of aseptic loosening due to bone failure. Moreover, the cementless TKA achieves bone ingrowth over a large implant surface to prevent concentration of forces and improves the ability of the implant to resist loosening.

As advantages, such as extended durability, short surgery time, potential bone preservation, and elimination of PMMA which may lead to embolization of bone marrow, have recently known, uncemented TKA is growing rapidly in popularity.

Nevertheless, uncemented or cementless TKA need improvements despite the aforementioned advantages. FIGS. 1 through 6 show issues that conventional uncemented TKA present. It is understood based on the drawings that initial implant fixation with stability is difficult.

The keel 32 provides excellent rotational stability in an conventional TKA tibial component 30, whereas coronal stability provided by the keel is unsatisfactory due to the keel being able to lift off the bone or the keel being vulnerable to forces exerted vertically as shown in FIG. 1. As shown in FIG. 2, sagittal plane stability is even more challenging due to roll back.

Moreover, as shown in FIG. 3, joint forces in the conventional femoral component are parallel to the fixation pegs and the implant may be in rocking motion, leading to bone ingrowth failure.

FIG. 4 shows a mimetic view illustrating insertion of the conventional tibial component 30. It can be seen from FIG. 4 that the tibia must be dislocated since the conventional tibial component 30 is loaded from the top, which complicates surgical procedures and is invasive.

As shown in FIGS. 5a and 5b, when the tibial component 30 should be removed for revision surgery, a metal plate on the tibia surface restricts access to the keel 32 and cutting through the keel 32 is challenging and creates a significant amount of metal debris. In such case, substantial bone loss can be accompanied if the tibial component 30 is forcefully extracted.

Bicruciate retaining TKA (BCR) is one type of TKA where anterior cruciate ligament (ACL) is preserved. BCR has advantages of natural knee motion, improved range of motion (ROM), and improved joint functions. As 70 to 80 percent of patients who receive TKA have normal anterior cruciate ligaments, a BCR tibial component is used in this case. As shown in FIG. 6, an conventional BCR tibial component 300 requires creation of cruciate bone island 1000. In the cruciate bone island 1000, corners (indicated by arrows) on the cruciate bone island 1000 create stress risers leading to avulsion fracture.

Thus, there is a need to develop a knee joint implant, capable of resolving aforementioned issues, providing stable fixing force and reducing bone removal.

SUMMARY OF THE INVENTION

Technical Problem

An object of the present invention is to provide a knee joint implant capable of resisting rotation, resisting external forces in coronal and sagittal planes, and providing stable fixing forces.

Another object of the present invention is to provide a knee joint implant which can simplify complex surgical procedures.

Yet another object of the present invention is to provide a knee joint implant which can minimize delay of recovery by reducing bone removal.

Yet another object of the present invention is to provide a knee joint implant which can minimize a surgical area by being slidably inserted to a bone from a side, simplify surgical procedures, and minimize bone loss during removal in revision surgery.

Yet another object of the present invention is to provide a knee joint implant where a tibial component can be inserted into the tibia without dislocating the femur by configuring the tibial component to be inserted from the side of the tibia.

Yet another object of the present invention is to provide a knee joint implant comprising a tibial component having a fixing portion being insertable from the side and reduced vulnerability to vertical fixing force.

Yet another object of the present invention is to provide a knee joint implant comprising a tibial component having resistance to pull-out from the tibia.

Yet another object of the present invention is to provide a knee joint implant capable of improving bone ingrowth.

Yet another object of the present invention is to provide a knee joint implant comprising a BCR tibial component being insertable from the side of the tibia.

Yet another object of the present invention is to provide a knee joint implant comprising a BCR tibial component having a fixing portion being insertable from the side of the tibia and improving the vertical fixing force.

Yet another object of the present invention is to provide a knee joint implant comprising a patellofemoral component having reduced vulnerability to the vertical fixing force by being inserted by slide fit.

Yet another object of the present invention is to provide a knee joint implant comprising a patella component capable of improving bone ingrowth and being stably fixed.

Yet another object of the present invention is to provide a knee joint implant comprising protrusion portion having parts gradually expanding and shrinking to be slidablely inserted from anterior direction or lateral-medial direction and prevent stress concentration.

Technical Solutions

The present invention has been made in an effort to solve the problems.

According to an embodiment of the present invention, a knee joint implant, comprising: a body portion including an articular surface and a contact surface formed on an opposite side of the articular surface; and a protrusion portion protruding from the contact surface and including a laterally expanded portion.

Preferably, the protrusion portion includes a first portion gradually expanding in a lateral direction and a second portion gradually shrinking in the lateral direction.

Preferably, the protrusion portion protrudes while forming a curved surface.

Preferably, the protrusion portion is a cylinder protruded from the contact surface.

According to another embodiment of the present invention, the implant is a tibial component, and the tibial component is inserted into a tibia in the lateral direction.

Preferably, the tibial component includes at least two protrusion portions, wherein the protrusion portions are formed at both sides.

Preferably, the tibial component protrudes substantially vertically from the contact surface and further comprises an extending portion disposed between the contact surface and the protrusion portion.

Preferably, the tibial component further comprises a pad disposed on an upper surface of the articular surface and made by polyethylene.

Preferably, spikes are formed on at least part of the surface of the protrusion portion.

According to another embodiment of the present invention, the implant is a femoral component, and the femoral component is inserted in a femur in the lateral direction.

Preferably, porous coating is applied to the surfaces of the contact surface and the protrusion portion.

Preferably, the femoral component further comprises a pair of protrusion portions, wherein the pair of the protrusion portions are insertable in the lateral direction into a fixing hole formed in the femur.

According to yet another embodiment of the present invention, the implant is a BCR tibial component, and the BCR tibial component is inserted into a tibia in the lateral direction.

Preferably, the implant further comprises a pair of BCR tibial components, wherein the pair of the BCR tibial components are insertable into fixing holes formed in the lateral and medial aspect of the tibia, respectively.

Preferably, the pair of the BCR tibial components includes a linkage buried in the tibia and connecting the pair of the BCR tibial components with each other.

Preferably, the linkage is formed as a curved shape or a V-shape.

According to yet another embodiment of the present invention, the implant is a patellofemoral component inserted into a femur in a direction parallel to a femoral surface.

Advantageous Effect

According to embodiments of the present invention, the present invention can obtain the following effects.

According to the present invention, provided is a knee joint implant capable of resisting rotation, resisting external forces in coronal and sagittal planes, and providing stable fixing forces.

According to the present invention, provided is a knee joint implant which can simplify complex surgical procedures.

According to the present invention, provided is a knee joint implant which can minimize delay of recovery by reducing bone removal.

According to the present invention, provided is a knee joint implant which can minimize a surgical area by being slidably inserted to a bone from a side, simplify surgical procedures, and minimize bone loss during removal in revision surgery.

According to the present invention, provided is a knee joint implant where a tibial component can be inserted into the tibia without dislocating the femur by configuring the tibial component to be inserted from the side of the tibia.

According to the present invention, provided is a knee joint implant comprising a tibial component having a fixing portion being insertable from the side and reduced vulnerability to vertical fixing force.

According to the present invention, provided is a knee joint implant comprising a tibial component having resistance to pull-out from the tibia.

According to the present invention, provided is a knee joint implant capable of improving bone ingrowth.

According to the present invention, provided is a knee joint implant comprising a BCR tibial component being insertable from the side of the tibia.

According to the present invention, provided is a knee joint implant comprising a BCR tibial component having a fixing portion being insertable from the side of the tibia and improving the vertical fixing force.

According to the present invention, provided is a knee joint implant comprising a patellofemoral component having reduced vulnerability to the vertical fixing force by being inserted by slide fit.

According to the present invention, provided is a knee joint implant comprising a patella component capable of improving bone ingrowth and being stably fixed.

BEST DESCRIPTION OF THE DRAWINGS

FIG. 7b shows an exploded perspective view of FIG. 8a;

FIG. 9b shows an exploded perspective view of FIG. 10a;

FIG. 14b shows an exploded perspective view of FIG. 17a;

FIG. 19b shows an exploded perspective view of FIG. 22a;

FIG. 22 shows a sectional view cut along A-A' represented in FIG. 21a.

DETAILED DESCRIPTION

Figure 1:
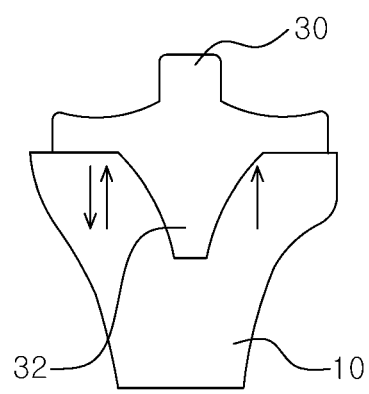
FIGS. 1 to 2 show issues that conventional TKA tibial components have.
Figure 2:
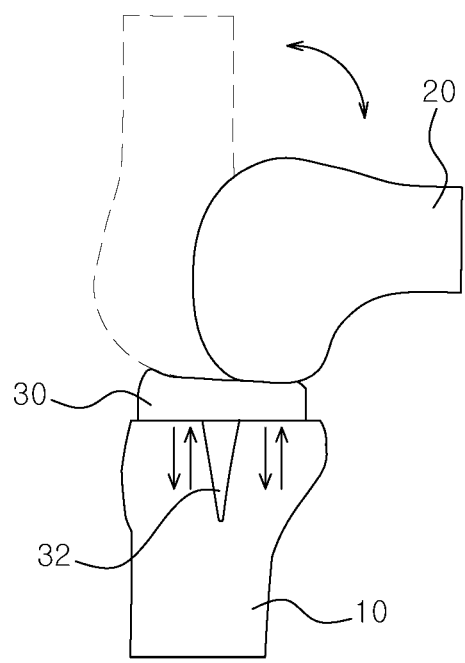
Figure 3:
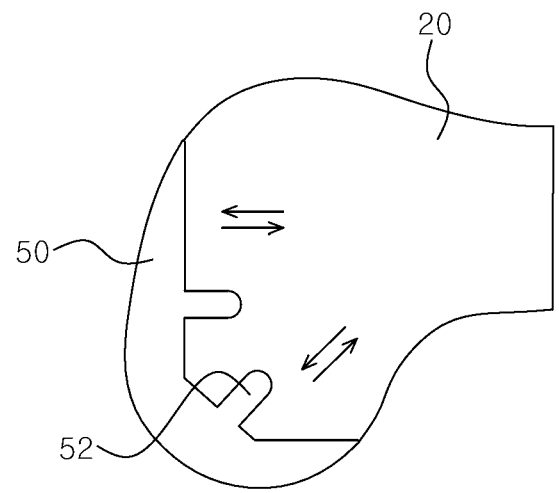
FIG. 3 shows an issue that conventional UKA femoral components have.
Figure 4:
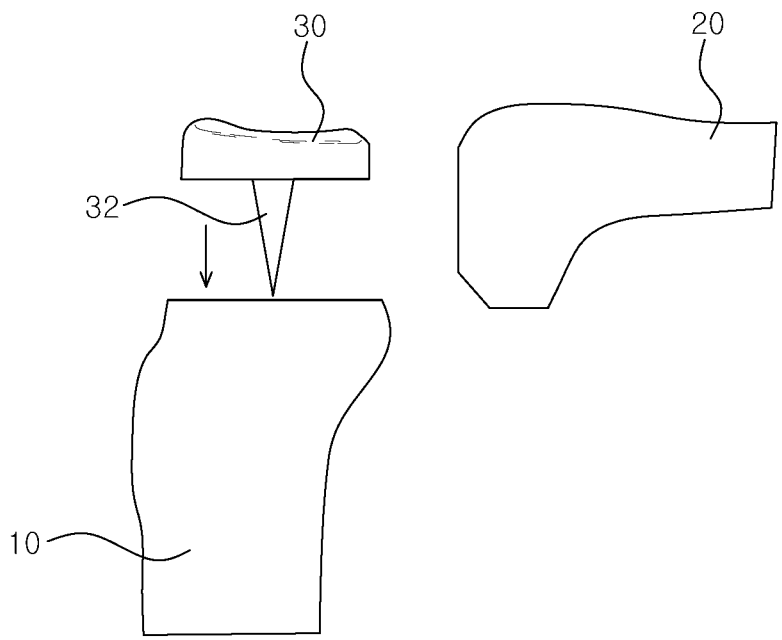
FIG. 4 illustrates a top loading method of the conventional TKA tibial components.
Figure 5A:
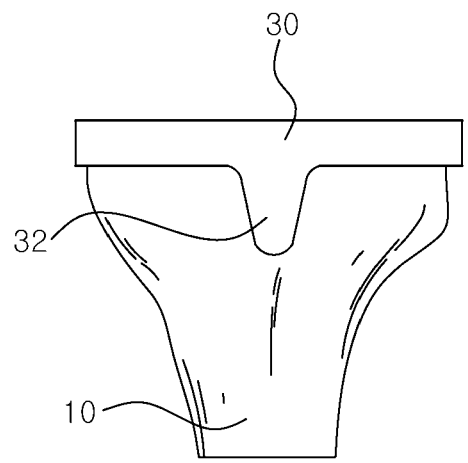
FIGS. 5a and 5b show issues that the conventional TKA tibial components have in revision surgery
Figure 5B:
Figure 6:
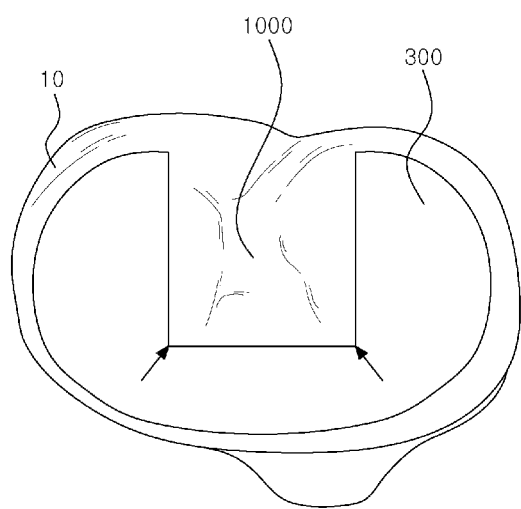
FIG. 6 shows issues that conventional BCR tibial components have.

Hereinafter, a knee joint implant according to the present invention is described in detail. Well-known functions or constructions will not be described in detail in case they may unnecessarily obscure the understanding of the present invention.

Specific structural and functional descriptions of embodiments of the present invention disclosed herein are only for illustrative purposes of the embodiments of the present invention. The embodiments according to the spirit and scope of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

The same reference numerals represent the same elements throughout the specification. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Below exemplary embodiments of the present invention are described in detail with reference to accompanying drawings. The invention may, however, be embodied in many different forms and should not be construed as being limited to the embodiments set forth herein; rather, these embodiments are provided so that this disclosure will be thorough and complete, and will fully convey the concept of the invention to those skilled in the art.

To solve the issues that prior art has, a knee joint implant according to the present invention comprises: a body portion including an articular surface and a contact surface formed in an opposite side to the articular surface; and a protrusion portion protruding from the contact surface and including a laterally expanded portion.

The knee joint implant according to the present invention may be any one of a TKA tibial component, a TKA femoral component, a BCR component, and a patellofemoral component, etc.

Figure 7A:
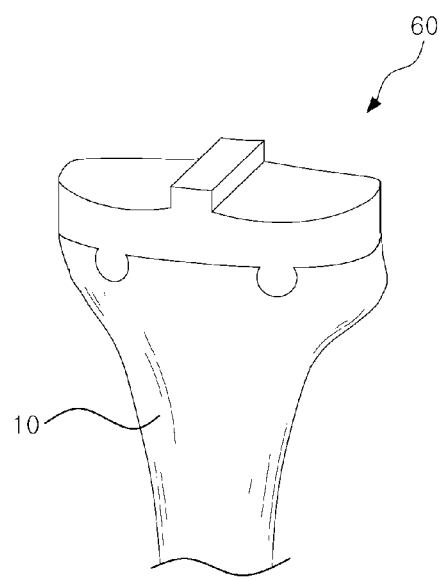
FIG. 7a shows a view of a TKA tibial component according to one embodiment of the present invention, coupled to the tibia.
Figure 7B:
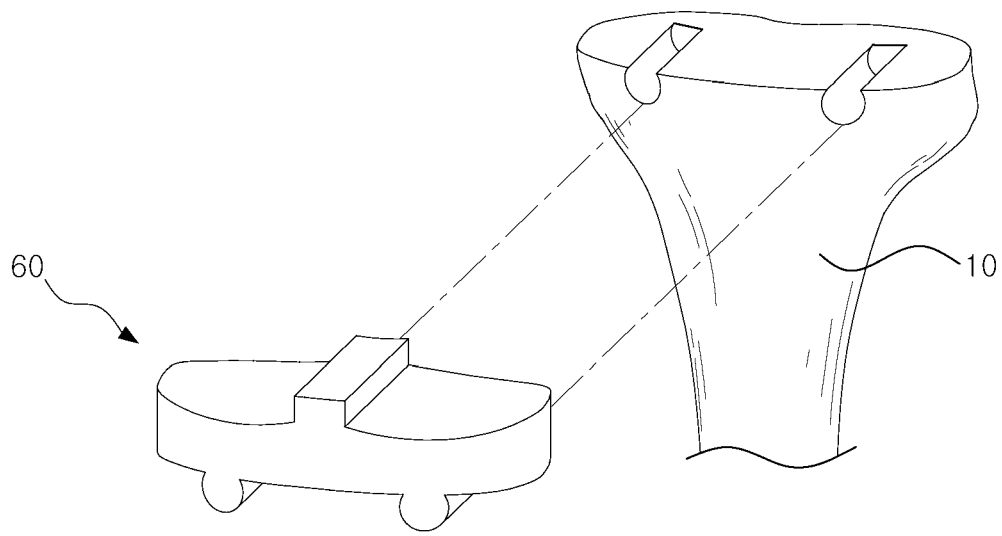

As shown in FIGS. 7a and 7b, the knee joint implant according to one embodiment of the present invention is the tibial component and may be a TKA tibial component 60.

Figure 8A:
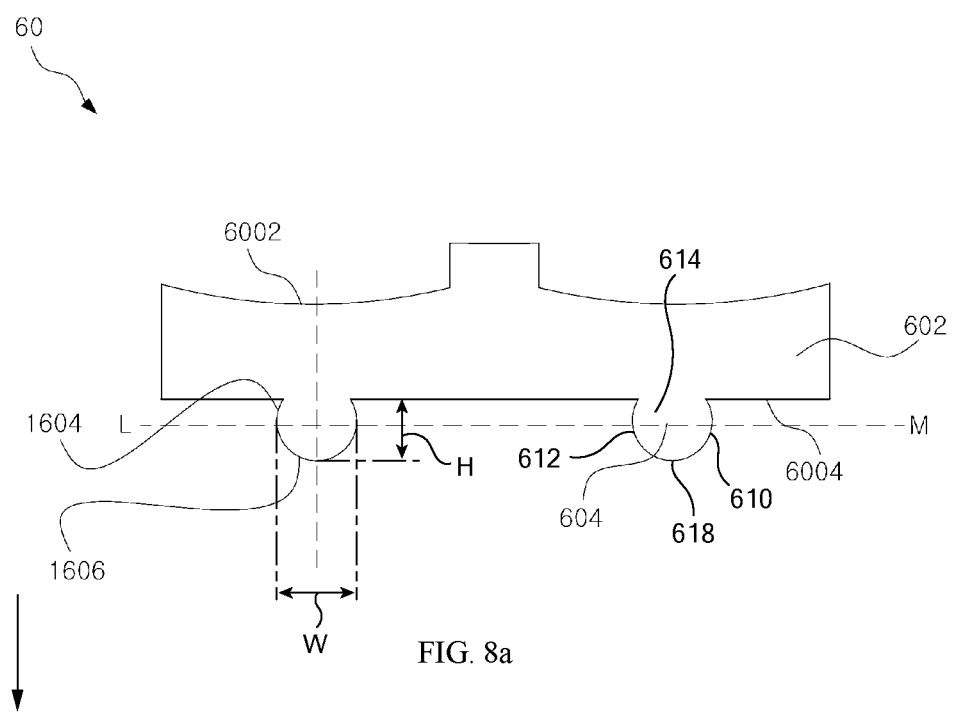
FIG. 8a shows a front view of the TKA tibial component according to one embodiment of the present invention.
Figure 8B:
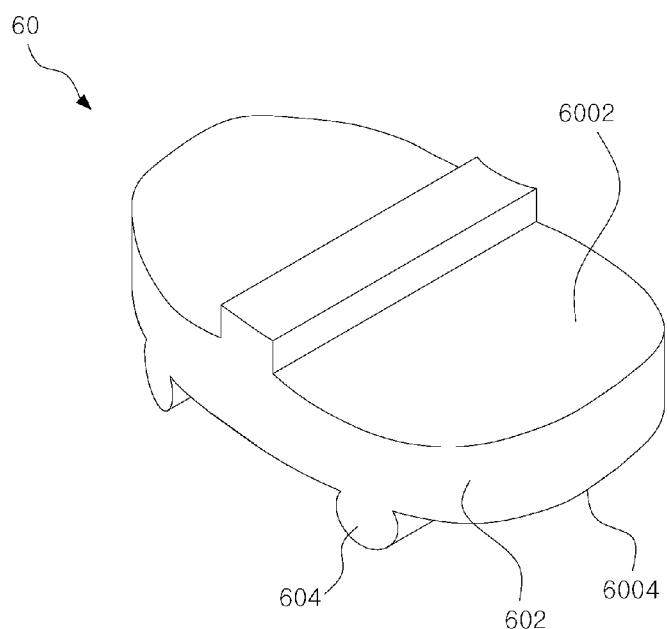
FIG. 8b shows a perspective view of the TKA tibial component according to one embodiment of the present invention.
Figure 8C:
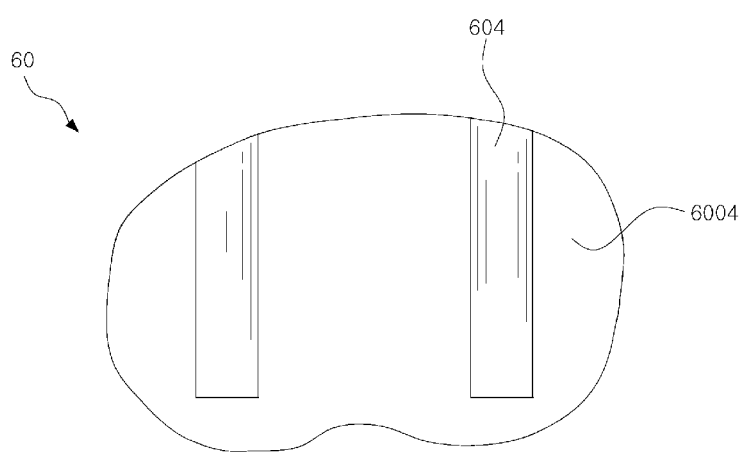
FIG. 8c shows a bottom view of the TKA tibial component according to one embodiment of the present invention.
Figure 9A:
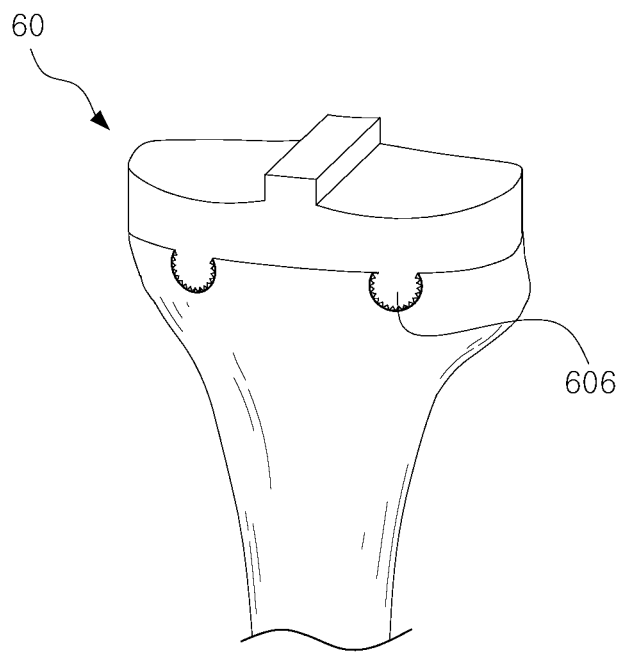
FIG. 9a shows a view of a TKA tibial component according to another embodiment of the present invention, coupled to the tibia.
Figure 9B:
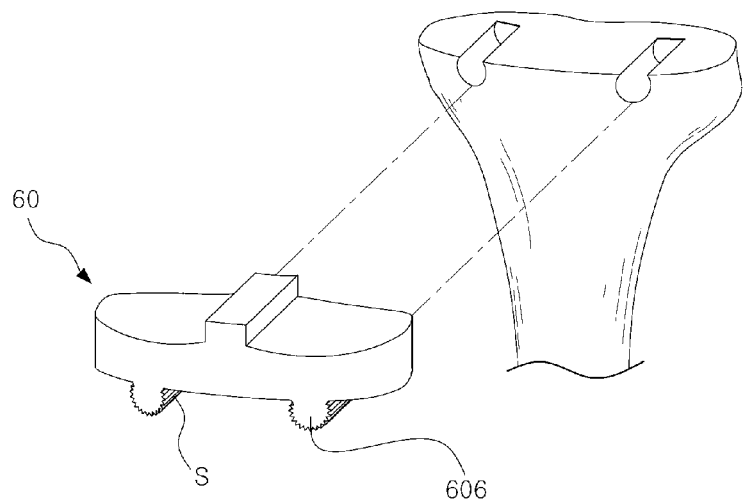

Referring to FIGS. 8a to 8c, the TKA tibial component 60 includes: a body portion 602 having an articular surface 6002 and a contact surface 6004 formed on an opposite side of the articular surface 6002. The body portion 602 replaces resected tibia 10, and the articular surface 6002 contacts with the femur (not shown) in an upper side and corresponds to a surface on which the femur articulates with respect to the tibial component. On the opposite side of the articular surface 6002, the contact surface 6004 contacting the tibia 10 is formed.

In addition, the TKA tibial component 60 includes a protrusion portion 604 protruding from the contact surface 6004 and including a laterally expanded part. In the TKA tibial component 60, two or more protrusions 604 may be formed at both sides.

The protrusion portion 604 is a portion which protrudes from the contact surface 6004 and is inserted in the bone. The protrusion portion 604 has a part where its width expands. Preferably, the protrusion portion 604 forms a curved surface and protrudes from the contact surface 6004. As shown in FIG. 8b, the protrusion portion 604 may comprise a first portion 1604 protruding from the contact surface 6004 and gradually expanding in the lateral direction; and a second portion 1606 protruding from the first portion 1604 and gradually shrinking in the lateral direction. For instance, the lateral direction means a lateral L-medial M line of the tibia, and the width of the protrusion portion 604 may be expanded in the L-M direction of the tibia. Accordingly, the TKA tibial component 60 may be inserted from the anterior aspect, not using the top loading method of the conventional tibia component as described above.

Figure 10A:
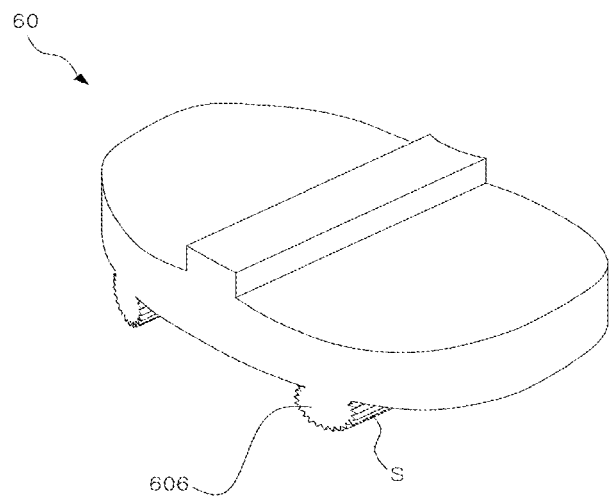
FIGS. 10a and 10b show a perspective view and a bottom view, respectively, of a TKA tibial component according to another embodiment of the present invention.
Figure 10B:
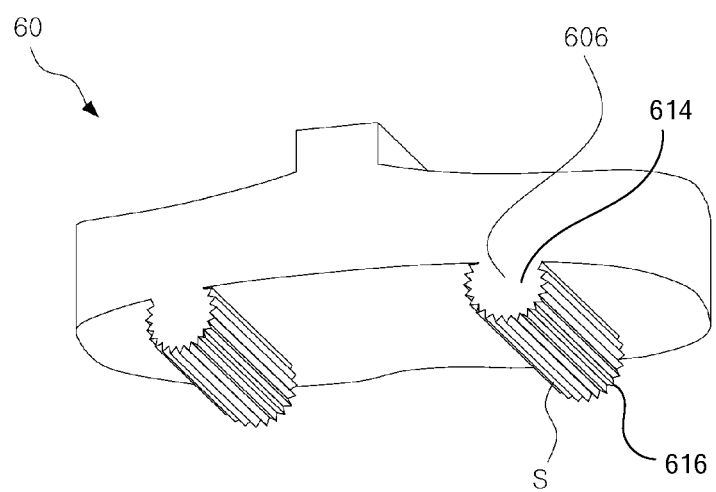

Expressed in other terms, with reference to FIG. 8a, protrusion portion 604 is elongated and is integrally formed with and extends from contact surface 6004. Protrusion portion 604 has opposing side faces 610 and 612 that extend longitudinally along contact surface 6004 between opposing end faces 614 and 616 (see FIG. 10b) and that outwardly project from contact surface 6004 to an outer face 618. Opposing side faces 610 and 612 are curved and extend linearly between opposing end faces 614 and 616. Opposing end faces 614 and 616 of protrusion portion 604 are openly exposed.

Protrusion portion 604 has a height H that extends between contact surface 6004 and outer face 618 and a width W that extends between the opposing side faces 610 and 612 along height H. Protrusion portion 604 has first portion 1604 wherein width W of protrusion portion 604 gradually laterally expands as protrusion portion 604 projects away from contact surface 6004 along a first section of height H. The width W of second portion 1606 of protrusion portion 604 gradually laterally constricts along a second section of height H, first portion 1604 being disposed between contact surface 6004 and second portion 1606. Protrusion portion 604 is freely disposed on contact surface 6004 so that no protrusions outwardly project from contact surface 6004 and intersect with protrusion portion 604.

As shown in the drawings, the width of the protrusion portion 604 may be expanded as the protrusion portion 604 protrudes from the body portion 602 and then shrunk. For instance, the protrusion portion 604 may be a cylinder or an elliptic cylinder protruding from the contact surface 6004. That is, the cross section of the protrusion portion 604 may be circular or elliptical and may take other shapes if the shape includes the first portion 1604 gradually expanding in the lateral direction and the second portion 1606 protruding from the first portion 1604 and gradually shrinking in the lateral direction.

A hole having a shape complementary to the protrusion portion 604 in the tibia, and the TKA tibial component 60 according to the present invention is inserted in the tibia by being inserted from the anterior aspect of the tibia. Accordingly, as the TKA tibial component 60 takes a lateral insertion method, not the top loading method of prior art, pull out strength of the tibial component is improved and stable fixing forces are provided.

The protrusion portion 604 may have various shapes if the protrusion portion 604 retains a region of increasing width as the protrusion portion 604 protrudes outward from the body portion 602. As shown in the drawings, it is preferable to form the protrusion portion as a cylinder. In case of a triangle or a dovetail shape, forming a fixing groove complementary to such shape during bone removal for inserting the protrusion portion 604 may be challenging, and stress may be concentrated on the bone as edged parts act as a notch or the bone may fracture. However, according to the present invention, since the cross section of the protrusion portion 604 is formed to have a curved surface, such as a circle, notches are not present and, thus, stress concentrations and bone fracture are prevented.

Moreover, since a center part of the protrusion portion 604 in the vertical direction is expanded the most, stable fixing forces are provided with respect to the tibia 10. As shown in FIG. 7b, the TKA tibial component 60 is inserted from the anterior aspect or the posterior aspect, which means the TKA tibial component 60 is not loaded from the top of the tibia. In other words, the TKA tibial component 60 is configured to be inserted in a horizontal direction. Accordingly, unlike the conventional tibial component, the protrusion portion 602 provides excellent resistance to vertically exerted forces and vertical fixing forces against force applied on the joint.

In addition, the contact surface 6004 and the protrusion portion 604 may be applied with porous coating, which induces bone ingrowth.

As shown in FIGS. 9a, 9b, 10a, and 10b, the protrusion portion 606 according to another embodiment of the present invention may include spikes S which extends from anterior side to posterior side and are formed on at least part of the surfaces. The spikes S may be formed on at least part of the surface of the protrusion portion 606 and on the entire surface of the protrusion portion 606. The spikes increase surface area of the protrusion portion 606 contacting the tibia and improves initial fixing force.

Figure 11:
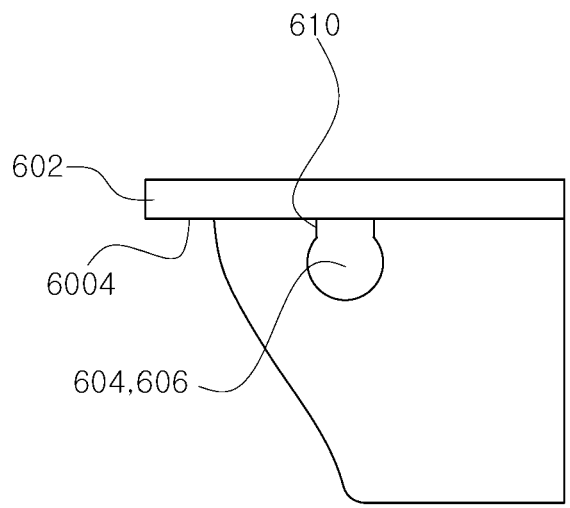
FIG. 11 shows a TKA tibial component according to another embodiment of the present invention.

Referring to FIG. 11, the TKA tibial component according to still another embodiment of the present invention further comprises an extending portion 610 disposed between the contact surface 6004 of the body portion 602 and the protrusion portions having a first portion 604 and a second portion 606. The extending portion 610 protrudes from the contact surface 6004 substantially perpendicularly and extends to a top surface of the first portion 604 gradually expanding in the lateral direction. Since the extending portion 610 moves fixing points away from the surface of the tibia, initial fixation can be improved. The pullout strength of the tibia component 60 can be improved if the extending portion 610 lengthens.

Figure 12:
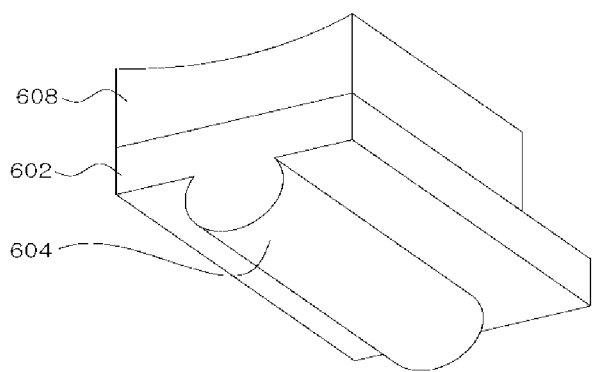
FIG. 12 shows a TKA tibial component according another embodiment of the present invention.

According to yet another embodiment of the present invention, the TKA tibial component further comprises a pad 608 disposed on an upper surface of the articular surface 6002 of the body portion 602 as shown in FIG. 12. The pad 608 includes an upper face acting as an articular surface, and the material may preferably be polyethylene. When the tibial component is made by titanium, polishing of the body portion 602 and cross-linked polyethylene pad 608 may be used to improve coupling with the pad 608.

Figure 13:
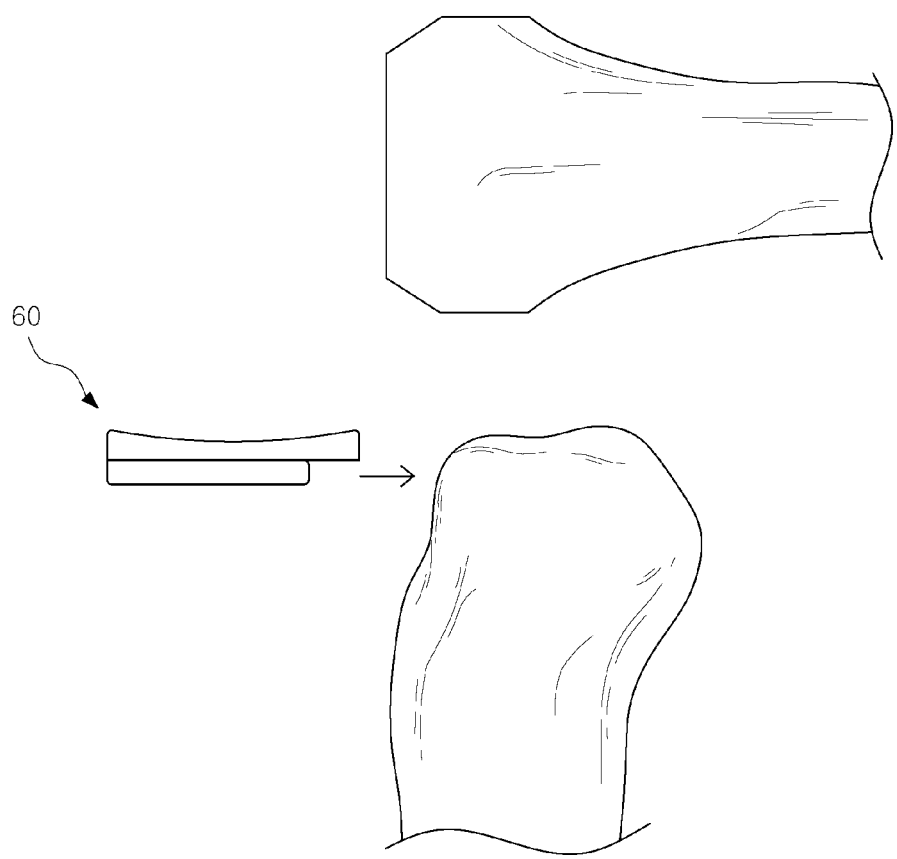
FIG. 13 shows a mimetic view illustrating insertion of the tibial component according to the present invention into the tibia.

FIG. 13 shows a mimetic view illustrating insertion of the tibial component 60 according to the present invention. The shape of the tibial component according to the present invention is suited to be slidingly inserted from anterior to posterior sides. The tibial component 60 can be inserted from the anterior side of the tibia without separating the tibia and the femur for access to an upper portion of the tibia. Thus, preservation of cruciate ligaments is facilitated and a surgical area is minimized.

Figure 14A:
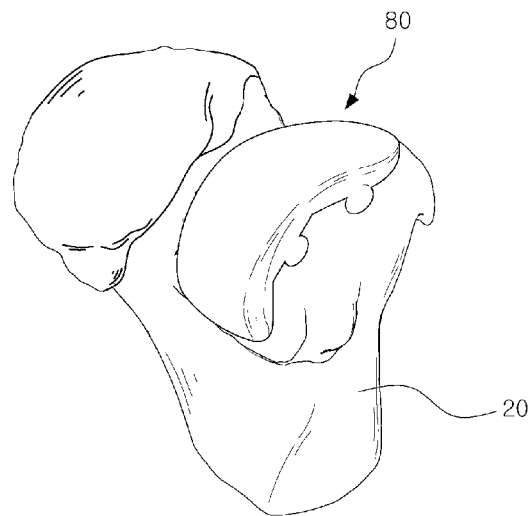
FIG. 14a shows a view of a UKA femoral component according to another embodiment of the present invention, coupled to the tibia.
Figure 14B:
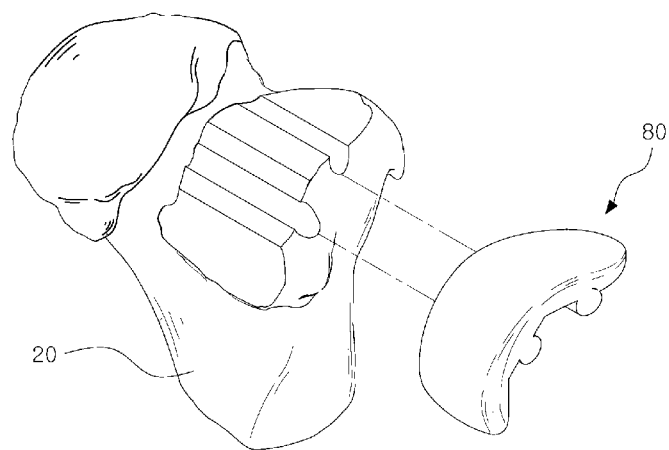

As shown in FIGS. 14a and 14b, the knee joint implant according to another embodiment of the present invention is the femoral component and may be any of the TKA femoral component and the UKA femoral component. Below the UKA femoral component 80 is described as an example.

Figure 15A:
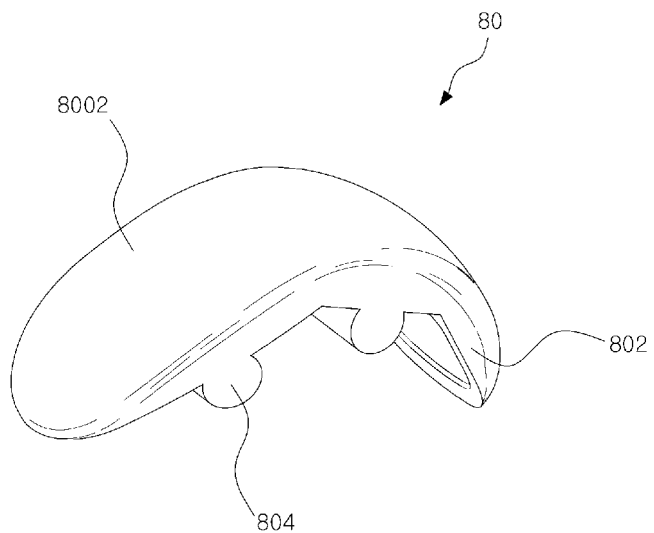
FIG. 15a shows a perspective view of the UKA femoral component according to another embodiment of the present invention.
Figure 15B:
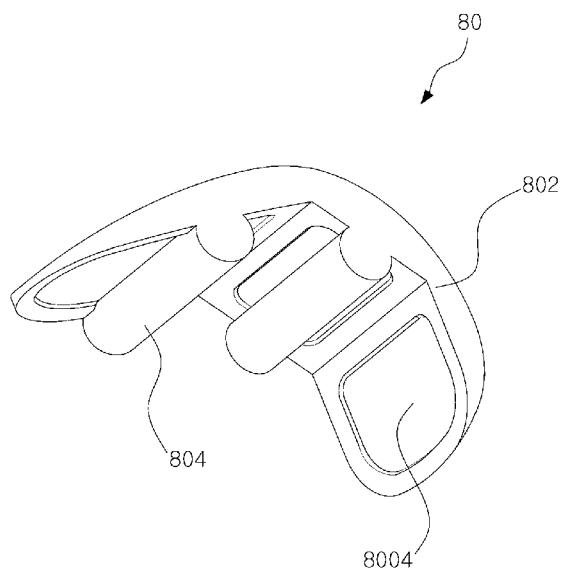
FIG. 15b shows a bottom view of the UKA femoral component according to another embodiment of the present invention.
Figure 15C:
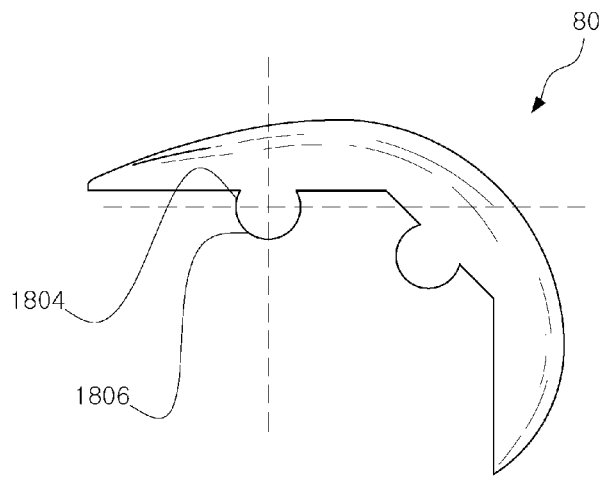
FIG. 15c shows a front view of the UKA femoral component according to another embodiment of the present invention.

Referring to FIGS. 15a to 15c the UKA femoral component 80 includes: a body portion 802 having an articular surface 8002 and a contact surface 8004 formed on an opposite side of the articular surface 8002. The body portion 802 replaces resected tibia 10, and the articular surface 8002 contacts with the tibia (not shown) in a lower side and corresponds to a surface on which the femur articulates with respect to the tibial component. On the opposite side of the articular surface 8002, the contact surface 8004 contacting the femur 20 is formed.

In addition, the UKA femoral component 80 includes a protrusion portion 804 protruding from the contact surface 6004 and including a laterally expanded part. In the UKA femoral component 80, two or more protrusion portions may be formed at both sides.

The protrusion portion 804 is a portion which protrudes from the contact surface 8004 and is inserted in the bone. The protrusion portion 804 has a part where its width expands. Preferably, the protrusion portion 804 forms a curved surface and protrudes from the contact surface 8004. The protrusion portion 804 may comprise a first portion 1804 protruding from the contact surface 8004 and gradually expanding in the lateral direction; and a second portion 1806 protruding from the first portion 1804 and gradually shrinking in the lateral direction. For instance, the later direction means a direction perpendicular to the protruding direction of the protrusion portion 804 from the contact surface 8004.

As shown in the drawings, the width of the protrusion portion 804 may be expanded as the protrusion portion 804 protrudes from the body portion 802 and then shrunk. For instance, the protrusion portion 804 may be a cylinder or an elliptic cylinder protruding from the contact surface 8004. That is, the cross section of the protrusion portion 804 may be circular or elliptical and may take other shapes if the shape includes the first portion 1804 gradually expanding in the lateral direction and the second portion 1806 protruding from the first portion 1804 and gradually shrinking in the lateral direction.

A hole having a shape complementary to the protrusion portion 804 in the femur, and the UKA femoral component 80 according to the present invention is inserted from the lateral or medial aspect of the femur. Accordingly, as the UKA femoral component 80 takes a lateral insertion method, pull out strength of the femoral component is improved and stable fixing forces are provided.

The protrusion portion 804 may have various shapes if the protrusion portion 804 retains a region of increasing width as the protrusion portion 804 protrudes outward from the body portion 802. As shown in the drawings, it is preferable to form the protrusion portion as a cylinder. In case of a triangle or a dovetail shape, forming a fixing groove complementary to such shape during bone removal for inserting the protrusion portion 804 may be challenging, and stress may be concentrated on the bone as cornered parts act as a notch or the bone may fracture. However, according to the present invention, since the cross section of the protrusion portion 804 is formed to have a curved surface, such as a circle, notches are not present and, thus, stress concentrations and bone fracture are prevented.

Moreover, since a center part of the protrusion portion 804 in the vertical direction is expanded the most, stable fixing forces are provided with respect to the femur 20. As shown in FIG. 18b, the UKA femoral component 80 is inserted from the lateral or medial aspect. In other words, the UKA femoral component 80 is configured to be inserted in a horizontal direction. Accordingly, the protrusion portion 804 provides excellent resistance to vertically exerted forces and vertical fixing forces against force applied on the joint, and sufficient stability against rocking forces. Also, although rocking motion occurs during roll back, the protrusion portion 804 provides resistance, thereby maintaining a stably fixed state. Besides, because the UKA femoral component 80 according to the present invention is inserted from the lateral or medial aspect, a resection area is small during surgery and the surgery is made simpler.

The protrusion portion 804 according to another embodiment of the present invention may include spikes formed on at least part of the surfaces. The spikes are formed for stable fixation. Specifically, the spikes improve coronal plane stability and provide resistance to rocking motion.

Figure 16:
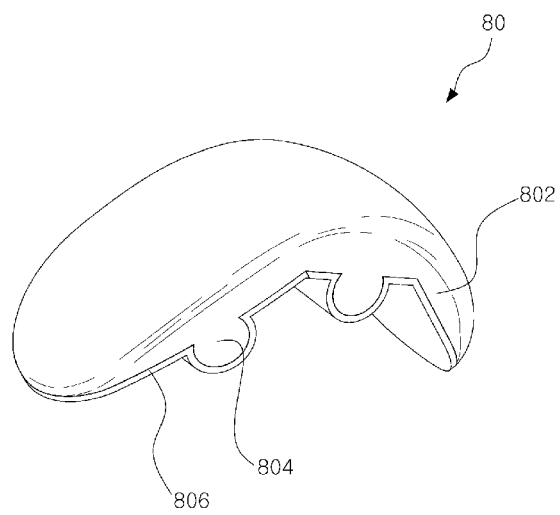
FIG. 16 shows a perspective view of the UKA femoral component according to another embodiment of the present invention.

Referring to FIG. 16, the UKA femoral component 80 according to another embodiment of the present invention further comprise a coating layer 806. The coating layer 806 is a porous coating layer capable of improving bone ingrowth. The coating layer 806 is preferably applied to the contact surface 8004 and the protrusion portion 804.

Various options for the material of the cementless UKA femoral component 80 may be considered. Cobalt-chromium with the beaded surface on the backside of implant may be least expensive and have a proven track record. In addition, titanium with titanium oxide surface may be considered, but oxide coating should be approximately 100 μm thick to avoid chipping concerns in this case. Moreover, cobalt-chromium with titanium plasma sprayed backside surface may be taken into consideration, but the possibility of surface delamination must be eliminated if this option is selected.

Figure 17A:
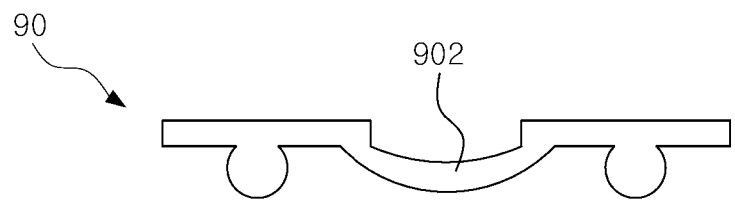
FIG. 17a shows a front view of a BCR tibial component according to yet another embodiment of the present invention.
Figure 17B:
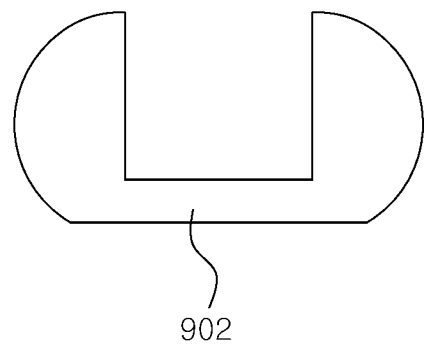
FIG. 17b shows a top view of a BCR tibial component according to yet another embodiment of the present invention.
Figure 17C:
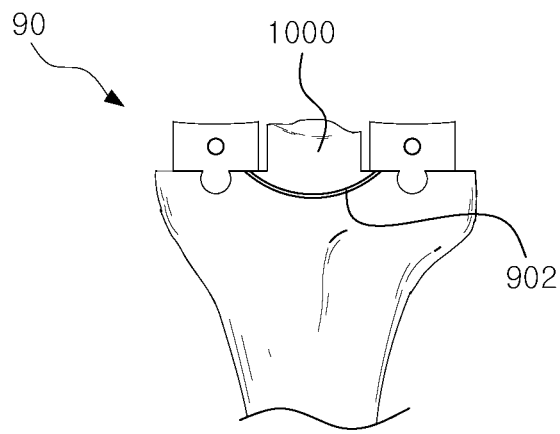
FIG. 17c shows a BCR tibial component according to yet another embodiment of the present invention, coupled to the tibia.

As shown in FIGS. 17a and 17c, the knee joint implant according to another embodiment of the present invention is the BCR tibial component 90 of the TKA tibial component.

Referring to FIGS. 17a to 17c, the BCR tibial component 90 includes: a body portion having an articular surface and a contact surface formed on an opposite side of the articular surface, and a linkage 902 connecting the body portion and buried in the tibia 10, and a protrusion portion.

The linkage 902 is formed to be buried in the tibia 10 such that the cruciate bone island extends from the posterior aspect to the anterior aspect of the tibia 10. The linkage may be a linkage 902 having a curved or arc shape. The dimensions of the linkage 902 buried in the tibia 10 may be determined based on required connection strength. As shown in FIG. 17c, the linkage 902 is buried in the tibia 10 such that the cruciate bone island 1000 extends from the posterior to the anterior aspects As described above, stress risers at the corners are problematic as the cruciate bone island 1000 is not formed from the anterior aspect to the posterior aspect but formed partly along the anterior to posterior tibia in prior art. However, in using the BCR tibial component 90 according to the present invention, the cruciate bone island 1000 extends from the posterior aspect to the anterior aspect of the tibia 10, thereby resolving the issue that the conventional implant presents. Accordingly, formation of the stress risers at the corners is avoided and avulsion fracture can be prevented.

Figure 18A:
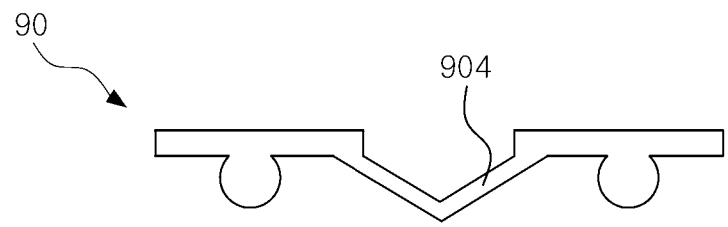
FIG. 18a shows a front view of a BCR tibial component according to yet another embodiment of the present invention.
Figure 18B:
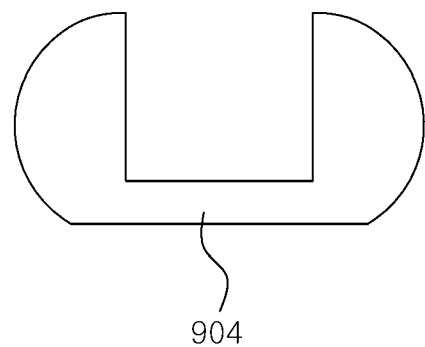
FIG. 18b shows a top view of a BCR tibial component according to yet another embodiment of the present invention.
Figure 18C:
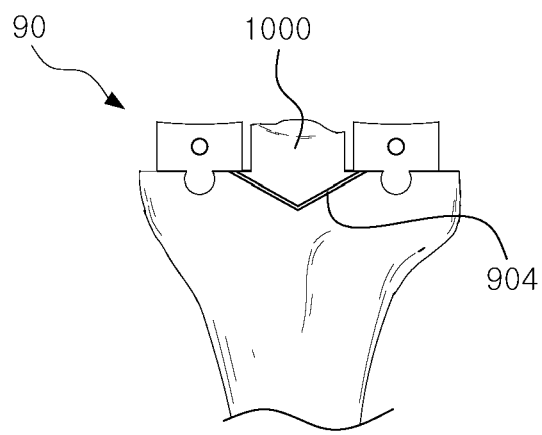
FIG. 18c shows a BCR tibial component according to yet another embodiment of the present invention, coupled to the tibia.

According to another aspect of the present invention, as shown in FIGS. 18a and 18b, the linkage may be a linkage 904 having a V-shape. The dimensions of the linkage 904 buried in the tibia 10 may be determined based on required connection strength. As shown in FIG. 18c, the linkage 904 is buried in the tibia 10 such that the cruciate bone island 1000 extends from the posterior to the anterior aspects. Accordingly, formation of the stress risers at the corners is prevented and avulsion fracture can be avoided.

According to the present invention, the BCR tibia component 90 can be inserted from the anterior side of the tibia without separating the tibia and the femur for access to an upper portion of the tibia. Thus, preservation of cruciate ligaments is facilitated and a surgical area is minimized. Also, according to various embodiments of the present invention, the problem of stress risers at sharp corners occurring in using the conventional BCR tibial component can be resolved.

Figure 19A:
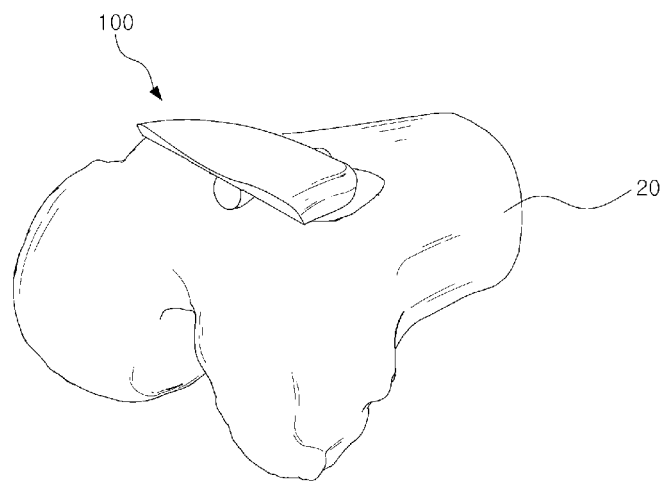
FIG. 19a shows a patellofemoral component according another embodiment of the present invention.
Figure 19B:
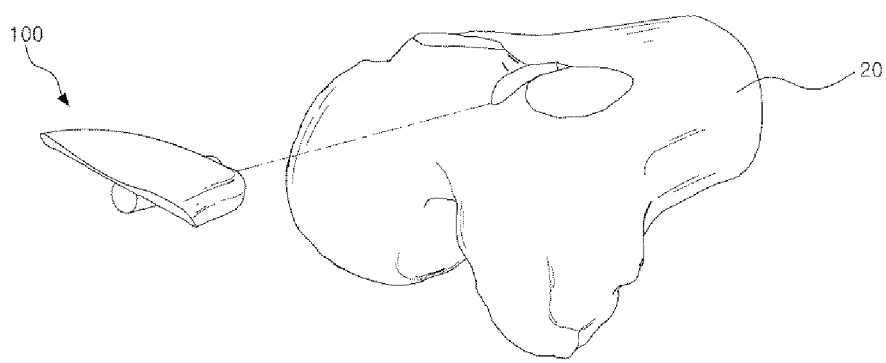

As shown in FIGS. 19a and 19b, the knee joint implant according to another embodiment of the present invention is the patellofemoral component 100.

Figure 20A:
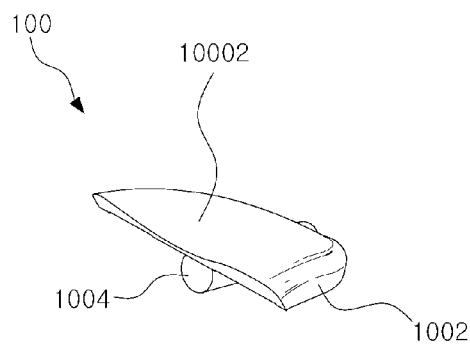
FIG. 20a shows a perspective view of a patellofemoral component according to another embodiment of the present invention.
Figure 20B:
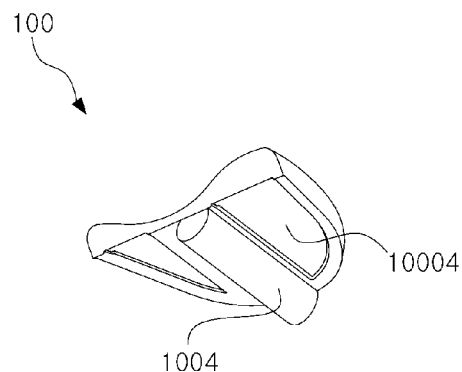
FIG. 20b shows a bottom view of a patellofemoral component according to another embodiment of the present invention.
Figure 20C:
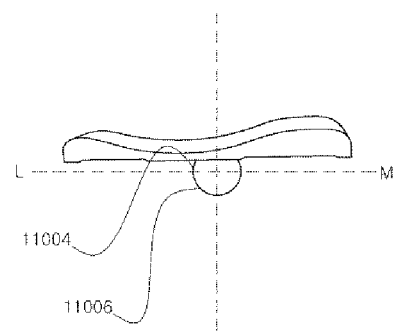
FIG. 20c shows a front view of a patella femoral component according to another embodiment of the present invention.

Referring to FIGS. 20a to 20b, the patellofemoral component 100 includes: a body portion 1002 having an articular surface 10002 and a contact surface 10004 formed on an opposite side of the articular surface 1002. The body portion 1002 replaces resected femur 20, and the articular surface 10002 corresponds to a surface on which the femur articulates with respect to the patella. On the opposite side of the articular surface 10002, the contact surface 10004 contacting the femur 20 is formed.

In addition, the patellofemoral component 100 includes a protrusion portion 1004 protruding from the contact surface 10004 and including a laterally expanded part.

The protrusion portion 1004 is a portion which protrudes from the contact surface 10004 and is inserted in the bone. The protrusion portion 1004 has a part where its width expands. Preferably, the protrusion portion 1004 forms a curved surface and protrudes from the contact surface 10004. The protrusion portion 1004 may comprise a first portion 11004 protruding from the contact surface 10004 and gradually expanding in the lateral direction; and a second portion 11006 protruding from the first portion 11004 and gradually shrinking in the lateral direction.

As shown in the drawings, the width of the protrusion portion 1004 may be expanded as the protrusion portion 1004 protrudes from the body portion 1002 and then shrunk. For instance, the protrusion portion 1004 may be a cylinder or an elliptic cylinder protruding from the contact surface 10004. That is, the cross section of the protrusion portion 1004 may be circular or elliptical and may take other shapes if the shape includes the first portion 11004 gradually expanding in the lateral direction and the second portion 11006 protruding from the first portion 11004 and gradually shrinking in the lateral direction.

A hole having a shape complementary to the protrusion portion 1004 is formed in the femur 20, and the patellofemoral component 100 according to the present invention is inserted in the femur 20 by being inserted from the distal femur. Accordingly, as the patellofemoral component 100 is slidingly fit in the femur, pull out strength of the tibial component is improved and stable fixing forces are provided.

The protrusion portion 1004 may have various shapes if the protrusion portion 1004 retains a region of increasing width as the protrusion portion 1004 protrudes outward from the body portion 1002. As shown in the drawings, it is preferable to form the protrusion portion as a cylinder. In case of a triangle or a dovetail shape, forming a fixing groove complementary to such shape during bone removal for inserting the protrusion portion 1004 may be challenging, and stress may be concentrated on the bone as cornered parts act as a notch or the bone may fracture. However, according to the present invention, since the cross section of the protrusion portion 1004 is formed to have a curved surface, such as a circle, notches are not present and, thus, stress concentrations and bone fracture are prevented.

Moreover, since a center part of the protrusion portion 1004 in the vertical direction is expanded the most, stable fixing forces are provided with respect to the femur 20. As shown in FIG. 22b, the patellofemoral component 100 is inserted along a direction parallel to the longitudinal cross section of the femur. Accordingly, the protrusion portion 1004 provides excellent resistance to vertically exerted forces and vertical fixing forces against force applied on the joint.

The knee joint implant according to the embodiments of the present invention provides stable fixation due to its shape. Also, the unique implant insertion method minimizes surgical areas and simplifies surgical procedures. Furthermore, bone removal can be reduced in knee joint implant surgery according to the present invention.

Figure 21A:
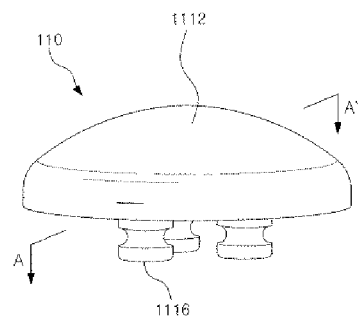
FIG. 21a shows a perspective view of a patellofemoral component according to another embodiment of the present invention.
Figure 21B:
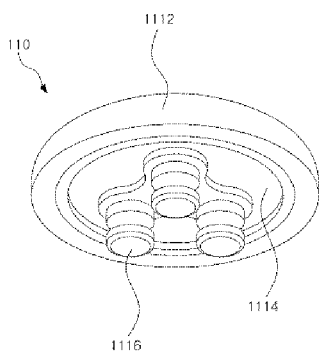
FIG. 21b shows a bottom view of a patellofemoral component according to another embodiment of the present invention.

As shown in FIGS. 21a and 21b, a patella component 110 according to another embodiment of the present invention may comprise: an articular surface 1112 and a support portion 1114.

The articular surface 1112 articulates with respect to the femur 20 and may be formed by polyethylene. Although conventional patella components are made entirely by polyethylene, only the articular surface 1112 at the outer side are made by polyethylene in the patella component 110 according to the present invention. Preferably, the thickness of the articular surface 1112 is 4-5 mm. Cross-linked polyethylene may be used as a material for the articular surface 1112, but this may cause a structural problem. Thus, it is preferable to use ethylene oxide sterilization.

Figure 22:
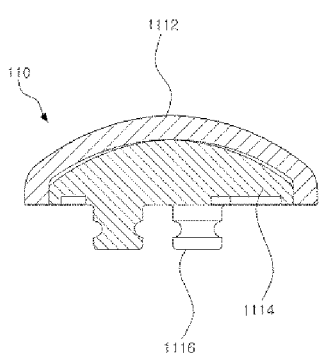

Referring to FIG. 22, the support portion 114 disposed inside the articular surface 1112 is coupled to the patella and includes one or more legs 1116 for coupling with the patella. The support portion 1114 is made by a metal, not polyethylene as in the conventional patella component. Also, a porous structure is formed on a coupling surface coupled to the patella, thereby inducing bone ingrowth and stable fixation.

In addition, the contour of the support portion 1114 is configured to correspond to the contour of the articular surface 1112. This removes stress risers and sufficiently supports the entire polyethylene.

In the above, the applicant described various embodiments of the present invention. It should be interpreted that such embodiments are merely examples which implement the technical idea and any modification or revision falls within the scope of the present invention if it implements the technical idea of the present invention, however.

REFERENCE NUMERALS

10: tibia
20: femur
30, 60: TKA tibial component
32: keel
50, 80: UKA femoral component
90, 300: BCR tibial component
100: patellofemoral component
110: patella component
602, 702, 802, 902, 1002: body portion
604, 606, 704, 804, 904, 1004: protrusion portion
608: pad
610: extending portion
806: coating layer
902, 904: linkage
1000: cruciate bone island
1112, 6002, 7002, 8002, 9002, 10002: articular surface
1114: support portion
1116: leg
6004, 7004, 8004, 9004, 10004: contact surface

The invention claimed is:

1. A knee joint implant, comprising:
a body portion including an articular surface and a contact surface formed on an opposite side of the articular surface; and
an elongated first protrusion being integrally formed with and extending from the contact surface, the first protrusion having opposing side faces, opposing end faces, and an outer face, wherein the opposing side faces extend longitudinally along the contact surface between the opposing end faces and outwardly project from the contact surface to the outer face, the first protrusion having a height that extends between the contact surface and the outer face and a width that extends between the opposing side faces along the height, the first protrusion having a first portion wherein the width of the first portion of the first protrusion gradually laterally expands as the first protrusion projects away from the contact surface toward the outer face, the first protrusion being freely disposed on the contact surface so that no additional protrusions outwardly project from the contact surface and intersect with the first protrusion,
wherein the implant is a femoral component, and the femoral component is configured to be inserted in a femur in a lateral direction.

2. The knee joint implant of claim 1, wherein the first protrusion further includes a second portion, a width dimension of the second portion gradually decreasing along a second section of the first protrusion, the first portion being disposed between the contact surface of the body portion and the second portion.

3. The knee joint implant of claim 1, wherein the opposing side faces of the first protrusion are curved.

4. The knee joint implant of claim 1, wherein the first protrusion has a cylindrical configuration.

5. The knee joint implant of claim 1, wherein spikes are formed on at least part of the first protrusion.

6. The knee joint implant of claim 1, further comprising a porous coating disposed on the contact surface and the first protrusion.

7. The knee joint implant of claim 1, further comprising a second protrusion projecting from the contact surface of the body portion, the second protrusion being spaced apart from and in parallel alignment with the first protrusion.

8. The knee joint implant of claim 7, wherein no additional protrusions outwardly project from the contact surface of the body portion and extend between the first protrusion and the second protrusion.

9. The knee joint implant of claim 1, wherein the opposing side faces of the first protrusion extend linearly between the opposing end faces.

10. The knee joint implant of claim 1, wherein the opposing end faces of the first protrusion are openly exposed.

* * * * *